United States Patent [19]

Gorsuch et al.

[11] Patent Number: 5,218,972
[45] Date of Patent: Jun. 15, 1993

[54] BIOMEDICAL FORCE MEASURING APPARATUS

[75] Inventors: Reynolds G. Gorsuch, Yountville; John Atkins, Corona Del Mar, both of Calif.

[73] Assignee: Healthdyne, Inc., Marietta, Ga.

[21] Appl. No.: 754,960

[22] Filed: Sep. 4, 1991

Related U.S. Application Data

[63] Continuation-in-part of Ser. No. 616,822, Nov. 19, 1990, abandoned, which is a continuation of Ser. No. 481,753, Feb. 15, 1990, abandoned, which is a continuation of Ser. No. 188,367, Apr. 29, 1988, abandoned.

[51] Int. Cl.$^5$ ..................... A61B 5/103; A61B 5/117
[52] U.S. Cl. ..................................... 128/775; 73/721; 73/727
[58] Field of Search ............... 128/632, 637, 672, 673, 128/675, 687, 689, 690, 748, 774, 775, 782; 73/721, 727, 754, 706, DIG. 4

[56] References Cited

U.S. PATENT DOCUMENTS

| 2,667,184 | 1/1954 | Hailer et al. | 73/706 |
| 3,897,682 | 8/1975 | Brooks | 128/654 |
| 4,576,181 | 3/1986 | Wallace et al. | 128/675 |
| 4,809,555 | 3/1989 | Kunz | 73/727 |

FOREIGN PATENT DOCUMENTS

| 215140 | 3/1987 | European Pat. Off. | 73/721 |
| 212890 | 8/1984 | Fed. Rep. of Germany | 73/706 |
| 3344799 | 6/1985 | Fed. Rep. of Germany | 73/721 |

*Primary Examiner*—Randy C. Shay
*Attorney, Agent, or Firm*—Jones & Askew

[57] ABSTRACT

A force transducer usable tokodynamometer for measuring intrauterine pressure and motion, and for measuring other force exerted by human body or other organisms. The tokodynamometer has a cavity filled with an incompressible fluid and closed by a flexible diaphragm disposed for contacting the body portion being studied. A zero-displacement fluid-pressure transducer is in the cavity and provides an electrical signal responsive to pressure in the fluid, as body force acts through the flexible diaphragm to induce pressure in the fluid. Changes in intrauterine pressure or other body forces are thus measured with no significant physical displacement of a transducer or other force-measuring element. The fluid-filled cavity has the shape of a truncated cone with the diaphragm at the larger end and the transducer at the smaller end, increasing the sensitivity of the transducer.

1 Claim, 1 Drawing Sheet

BIOMEDICAL FORCE MEASURING APPARATUS

CROSS-REFERENCE TO RELATED APPLICATIONS

This is a continuation-in-part of Ser. No. 07/616,822 filed Nov. 19, 1990, now abandoned, which is a continuation of Ser. No. 07/481,753 filed Feb. 15, 1990 and now abandoned, which in turn is a continuation of Ser. No. 07/188,367 filed Apr. 29, 1988 and now abandoned.

FIELD OF INVENTION

This invention relates in general to apparatus for measuring force, and relates in particular to a dynamometer for measuring the force exerted by selected portions of the human body or other organisms.

BACKGROUND OF THE INVENTION

During the normal delivery and birthing process, most obstetricians monitor the intrauterine pressure of the obstetrics patient. These various pressure measuring devices detect changes in the intrauterine pressure, usually caused by the onset of contractions during birth.

In the past, intrauterine pressure was measured by catheters, balloons and pressure transducers introduced into the uterus. These devices gave generally accurate relative pressure readings; however, they were invasive and caused much discomfort to the obstetrics patient.

Recently, a noninvasive method of measuring intrauterine pressure has been developed. The apparatus for practicing this noninvasive method is termed a "tokodynamometer". By pressing a flat plate on the outside surface of the abdomen, the wall of the abdomen turns into a flat diaphragm. A pressure sensitive area is located in the center region of the plate and moves in response to the corresponding intrauterine pressure exerting force upon the pressure sensitive area on the plate. A strain gauge transducer produces an output signal responsive to the movement of the pressure sensitive area, and that signal thus generally indicates the intrauterine pressure producing the force-related signal.

The foregoing kind of tokodynamometer is the subject of U.S. Pat. No. 4,640,295 to Isaacson and an article entitled "The GuardRing Tokodynamometer", by C. N. Smythe, *Journal of Obstetrics and Gynecology*, Volume 64, pages 59–66, (1957). However, these tokodynamometers have not been found useful to accurately measure intrauterine pressure. Tokodynamometers of the kind shown in the foregoing patent rely on a force summing element which requires mechanical movement to operate a strain gauge or other displacement-driven transducer. The mechanical displacement required by the force-summing element and by the transducer itself reduced the linearity of the measuring devices, and adversely affected calibration to such an extent that they are not useful for measuring absolute force. Consequently, the prior apparatus is only accurate with respect to periodicity of contractions, but not for the absolute amplitude thereof.

There is, accordingly, a need for a tokodynamometer which accurately measures intrauterine pressure and movement in addition to periodicity of contractions. Moreover, if the accurate intrauterine pressure is measured, the force responsible for this pressure can then be integrated to calculate the total work of a contraction and display this calculation for the obstetrician to see as the contraction occurs.

SUMMARY OF THE INVENTION

Stated in general terms, the force measuring apparatus of the present invention receives force exerted on the apparatus by a human body or other biological organism and couples that force to an incompressible fluid confined in a space. The pressure in the fluid thus is a function of intrauterine pressure or other bodily force acting on the incompressible fluid. A zero-displacement transducer coupled to the fluid responds to the pressure in the incompressible fluid and produces a signal proportional to the body force creating the pressure in the fluid. Neither the fluid nor the pressure transducer coupled to the fluid undergoes any substantial movement in response to applied forces over the full measuring range of the force measuring apparatus, avoiding or greatly alleviating the problems of linearity and calibration encountered with prior-art tokodynamometers and the like. The signal produced by the transducer is proportional to the absolute force exerted on the measuring apparatus by the body. This signal can be processed and displayed so that the obstetrician or other investigator can see the periodicity of contractions and the total work of contractions or other bodily force acting on the apparatus.

Stated somewhat more particularly, the zero-displacement transducer is rigidly mounted in fluid pressure communication with a chamber filled with an incompressible fluid. A flexible diaphragm, disposed for contacting the body portions undergoing examination, couples the body forces to the fluid so that the fluid pressure varies in response to the applied force. The area of the diaphragm preferably is greater than the force-summing area of the pressure transducer, increasing the sensitivity of the apparatus. Because the transducer exhibits virtually no displacement while measuring variation in the fluid pressure, the full range of force-related pressure measurement is obtained and an accurate absolute reading of intrauterine pressure or other body force or force-inducing movement is achieved. Henceforth, the total work exhibited by each uterine contraction can be calculated by integrating the area under the force vs. time curve.

Accordingly, it is an object of the present invention to provide an improved biomedical force measuring apparatus.

It is another object of the present invention to provide a biomedical force measuring apparatus which is linear and exhibits low volumetric displacement of the pressure sensor.

It is yet another object of the present invention to provide an improved tokodynamometer for measuring periodicity and amplitude of contractions during birth.

It is still a further object of the present invention to provide a tokodynamometer which provides a force-responsive output useful for determining the total work of contractions.

The object and nature of the present invention will become more readily apparent from the following description of a preferred embodiment.

DETAILED DESCRIPTION OF PREFERRED EMBODIMENT

Figure 1:
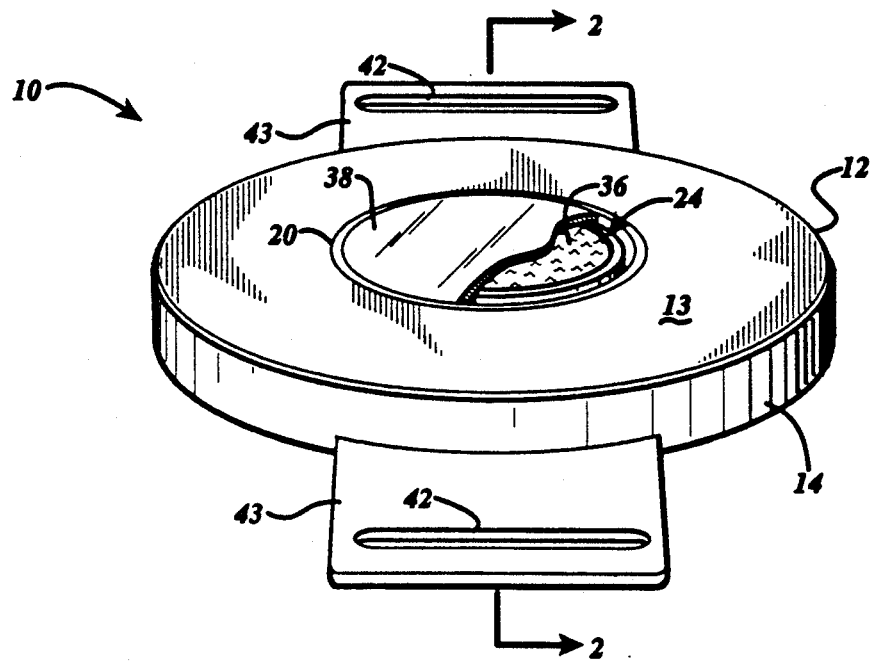
FIG. 1 is a pictorial view, partially broken away for illustration, showing a preferred embodiment of a tokodynamometer constructed in accordance with the present invention.

Turning first to FIG. 1, there is shown generally at 10 a tokodynamometer comprising a rigid circular housing 12 having a flat front surface 13 extending radially outwardly to join the cylindrical hoop 14 extending axially a short distance to define the hollow interior 15 (FIG. 2) of the housing. A removable cover plate 16 closes the interior 15 of the housing 12 on the end opposite the front surface 13. An annular rib 17 on the inside of the front surface 13 extends concentric to the axis of the housing and abuts the confronting inner surface 18 of the cover plate 16 for structural rigidity of the assembled tokodynamometer.

The front surface 13 has an axial circular opening 20 within which is fitted the guide 22 in the shape of a hollow truncated cone. The open interior of the guide 22 defines a cavity 24 open to the front surface 13 and extending rearwardly within the housing. A pressure transducer 26 is affixed at the bottom of the guide 22 and effectively closes the open bottom 28 of the cavity 24. The transducer 26 preferably is of a kind known as zero-displacement transducers, wherein electrical signals corresponding to the full nominal range of pressure measurement are produced with physical movement limited to the microinch range. An example of such a transducer is a solid-state pressure transducer manufactured by Motorola and producing digital electrical output signals on the signal line 44 in response to sensed fluid pressure. The back of the transducer 26 abuts the surface 18 of the cover plate, so that the transducer is held firmly in place between the cover plate and the guide 22.

The guide 22 has a flanged upper end 32 which fits within the opening 20 flush with the front surface 13 of the housing. The opening 34 at the upper end 32 of the conical cavity 24 at the front surface 13 is substantially larger than the open bottom 28 contacting the transducer 26, so that the area of the upper opening is greater than the area of the open bottom. The guide 22 is inelastic and undergoes no expansion in response to fluid pressures anticipated within the cavity 24.

A noncompressible fluid 36 fills the cavity 24, making contact with the transducer 36 at the bottom of the cavity. The fluid 36 is a gel-cured silicone, in an actual embodiment of the invention. A flexible diaphragm 38 covers the cavity 24 in intimate contact with the noncompressible fluid 36 in the cavity. The diaphragm also may be of silicone for acceptable flexibility and inertness, as the diaphragm contacts the abdomen or other portions of the body undergoing examination by the tokodynamometer. The diaphragm 38 is substantially flush with the front surface 13 and has a peripheral inwardly-facing coaxial flange 39 fitting into a mating annular slot 40 formed in the guide 22 surrounding the opening 34 of the guide.

The diaphragm 38 preferably is relatively stiff in its dimension of thickness, so that bodily forces acting perpendicular to the diaphragm are transmitted therethrough to the underlying incompressible fluid 36 without significantly compressing the diaphragm itself. However, it will be understood that the overall diaphragm 38 should be sufficiently flexible to transmit bodily force to the incompressible fluid without offering substantial resistance to that force. The range of such flexibility is permissibly small because the pressure transducer 26 undergoes little or no displacement in response to pressure changes in the incompressible fluid within the cavity 24.

The plate 16 is attached to the back of the housing 12 by fasteners such as screws (not shown) or the like, has a pair of strap-affixing slots 42 formed in tabs 43 extending beyond the profile of the housing 12. The signal line 44 is connected to the transducer 16 and extends outside the housing 12 to a suitable connector.

The operation of the present embodiment is now described. The tokodynamometer 10 is positioned on the top of the abdomen of the obstetric patient. The tokodynamometer 10 is then secured in place on the abdomen by a strap extending through the slots 42 and around the body of the patient in the usual manner. The flat surface of the housing 12, and in particular the flexible diaphragm 38 formed in the flat surface 13 and covering the cavity 24, thus firmly contact the abdomen, and the force exerted against the diaphragm by the abdomen is transmitted through the diaphragm to exert pressure in the incompressible fluid 36 within the cavity. This fluid pressure is sensed by the transducer 26, which produces an output signal corresponding to the sensed fluid pressure and thus corresponding to the abdominal pressure creating the fluid pressure. When a uterine contraction takes place, the increased force is exerted upon the diaphragm 38, causing an increased fluid pressure then transmitted to the transducer 26. The transducer output signals corresponding to the force of contraction are then displayed upon a screen or other suitable apparatus for the obstetrician to see and analyze. The cover plate 16, which is secured to the housing 12 and firmly urged into contact with the ribs 17, keeps the transducer 26 from moving relative to the housing 12 so that all changes in force accurately produce corresponding pressure changes in the noncompressible fluid within the cavity 24.

Figure 2:
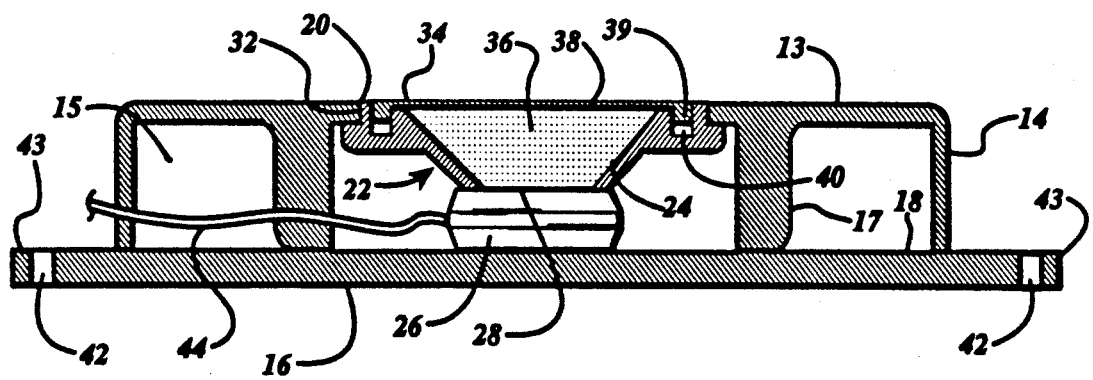
FIG. 2 is a section view along line 2—2 of FIG. 1.

The surface area of the diaphragm 38 is substantially larger than that of the pressure transducer 26, as best shown in FIG. 2. The larger surface area exposed to the skin of the maternal abdomen provides a larger sensing area to detect motions beneath the skin, and the ratio of the larger sensing area to the relatively smaller summation area of the transducer 26, located immediately beneath the open bottom 28 of the guide 22, increases the sensitivity of the overall tokodynamometer 10 through a form of hydraulic leverage. The use of a sensing area larger than the transducer summation area makes the present tokodynamometer capable of improved detection of fetal movements.

Because the transducer output signals represent the absolute value of force producing the pressure in the incompressible fluid within the cavity, the output signals can be integrated to determine the work performed in each contraction. Other signal processing techniques known to those skilled in the art are also applicable.

The present biomedical force measuring apparatus is not limited to obstetrical uses. Examples of other possible applications are measuring intradural pressure of head trauma, and measuring esophageal motility. It should be understood that the present apparatus also is useful to measure motion of a body region exerting changing force on the diaphragm 38 of the tokodynamometer 10.

It should be understood that the foregoing relates only to a preferred embodiment of the present invention, and that numerous changes and modifications therein may be made without departing from the spirit and scope of the invention as defined in the following claims.

What is claimed is:

1. A biomedical apparatus for measuring the amount of force exerted on an external surface of a body in response to activity within the body, comprising:
   a housing having a rigid surface operative to be maintained in contact with a selected portion of the body surface, and comprising an interior region beneath the surface;
   an opening in the surface of the housing;
   a chamber communicating with the opening and containing an incompressible gel;
   a flexible yet substantially noncompressible diaphragm disposed on the opening for contact by the portion of the body surface, and in force transfer relation with the gel in the chamber, so that the force exerted against the housing by the body is transferred by the diaphragm to the gel to induce hydrostatic pressure therein;
   the chamber being substantially frustoconical in shape and narrowing from a first portion communicating with the opening in the surface to a terminal portion housing a second opening of reduced area relative to the opening in the surface;
   a pressure transducer disposed to close the second opening in pressure responsive relation to the hydrostatic pressure in the gel at the second opening and operative to provide a signal corresponding to such pressure;
   means associated with the housing holding the transducer rigidly in place relative to the chamber so that the transducer remains stationary notwithstanding changes in the fluid pressure within the chamber;
   the means comprising a rigid member secured to the housing and extending behind the terminal portion of the chamber to engage the transducer between the means and the terminal portion; and
   an annular rib in radial spaced relation to the chamber and abutting the rigid member for structural rigidity of the housing;
   whereby the transducer signal is a function of the force exerted on the body surface and amplified by the ratio of areas of the first-mentioned and second openings.

* * * * *